United States Patent [19]

Adaway et al.

[11] Patent Number: 5,688,953
[45] Date of Patent: Nov. 18, 1997

[54] PROCESS FOR THE PREPARATION OF 3,3, 5-TRICHLOROGLUTARIMIDE

[75] Inventors: Timothy J. Adaway; Larry D. Kershner, both of Midland, Mich.

[73] Assignee: DowElanco, Indianapolis, Ind.

[21] Appl. No.: 690,722

[22] Filed: Jul. 31, 1996

[51] Int. Cl.$^6$ .................. C07C 211/02; C07C 211/38
[52] U.S. Cl. .................. 546/243; 546/250; 546/249; 546/294; 546/345
[58] Field of Search .................. 546/243, 250, 546/294, 345

[56] References Cited

U.S. PATENT DOCUMENTS

| | | | |
|---|---|---|---|
| 2,673,205 | 3/1954 | Hoffmann et al. | 260/281 |
| 2,848,455 | 8/1958 | Hoffmann et al. | 260/281 |
| 4,245,098 | 1/1981 | Steiner | 546/250 |
| 4,327,216 | 4/1982 | Martin | 546/250 |
| 4,360,676 | 11/1982 | Martin et al. | 546/243 |
| 4,400,202 | 8/1983 | Teach | 71/94 |
| 4,469,896 | 9/1984 | Steiner | 568/495 |
| 4,595,408 | 6/1986 | Teach | 71/94 |
| 4,612,312 | 9/1986 | Hibert et al. | 514/225 |
| 4,996,323 | 2/1991 | Pews | 546/250 |
| 5,017,705 | 5/1991 | Becker | 546/250 |
| 5,071,857 | 12/1991 | Foster et al. | 514/318 |
| 5,591,857 | 1/1997 | Friis et al. | 546/296 |

FOREIGN PATENT DOCUMENTS

| | | |
|---|---|---|
| WO 94/14774 | 7/1994 | WIPO. |
| WO 95/06639 | 9/1995 | WIPO. |

OTHER PUBLICATIONS

"Analogs of the Abortifacient Aminoglutethimide", R. Paul, et al., Journal of Medicinal Chemistry, 1974, vol. 17, No. 5, pp. 539–541.

"Synthesis and Antihypertensive Properties of New 3–Hydrazinopyridazine Derivatives", G. Pifferi et al., Journal of Medicinal Chemistry, 1975, vol. 18, No. 7, pp. 741–746.

"A reinvestigation of the synthesis of 1,2–dihydro[1,2] diazpin–3–ones from pyrones", N. Peet et al., Chemical Abstracts, vol. 106, 1987, p. 584, 106:84339k.

"Uber Alkylenimin–Derivate", E. Tagmann t al., Helvetica Chimica Acta, Volumen XXXV, Fasciculus v (1952)–No. 195, pp. 1541–1548.

"Substances Acting on the Central Nervous System. III. Synthesis of the Racemic and Optically Active 2–Ethyl–2–phenylglutarimide", S Kukolja et al., Croatica Chemica Acta, 33, (1961), pp. 41–44.

"Biologische Abbauversuche III). Uber die Synthese einiger Glutarsaureimide)", K. Hoffman et al., Helvetica Chimica Acta, Volumen XL, Fascibulus II (1957) –No. 46–47, pp. 387–403.

"Halogenierte Pyridine I. Die Herstellung von 3–Halogenmethylpyridinen aus dimerem Acrylnitril", Hans Fritz et al., Helvetica Chimica Acta –vol. 59, Fasc. 1 (1976) –Nr. 19–20, pp. 179–190.

*Primary Examiner*—Shailendra Kumar
*Attorney, Agent, or Firm*—Richard T. Knauer

[57] ABSTRACT

3,3,5-Trichloroglutarimide is prepared by combining 4-cyano-2,2,4-trichlorobutanoyl chloride with water in an inert organic solvent at a temperature between about 20° C. and about 50° C. to obtain a mixture of 3,3,5-trichloroglutarimide and 3,3,5,6-tetrachloro-5,6-dihydropyridin-2-one. The 3,3,5,6-tetrachloro-5,6-dihydropyridin-2-one is then heated in the presence of water and inert organic solvent to between about 90° C. and about 100° C. to convert the 3,3,5,6-tetrachloro-5,6-dihydropyridin-2-one to 3,3,5-trichloroglutarimide.

5 Claims, No Drawings

PROCESS FOR THE PREPARATION OF 3,3,5-TRICHLOROGLUTARIMIDE

FIELD OF THE INVENTION

The present invention relates to a process for the preparation of 3,3,5-trichloroglutarimide wherein a 2,2,4-trichloro-4-cyanobutyric acid derivative is converted to the desired glutarimide compound.

BACKGROUND OF THE INVENTION 2,3,5,6-Tetrachloropyridine and 3,5,6-trichloropyridin-2-ol obtainable therefrom by hydrolysis are valuable intermediates for producing various active substances, particularly insecticides, herbicides and fungicides (see, for example, U.S. Pat. Nos. 4,133,675, 3,244,586, 3,355,278 and 3,751,421; French Patent Specification No. 2,171,939 and also J. Agr. Food Chem. 14, 304 (1966)). The processes known for producing 2,3,5,6-tetrachloropyridine are in various respects unsatisfactory. 2,3,5,6-Tetrachloropyridine can be obtained by high-temperature chlorination (about 200°–600° C., preferably about 350°–600° C.) of pyridine or of pyridine derivatives, such as 3,5-dichloropyridine. Such high-temperature processes are usually not selective as they typically result in the formation of other highly chlorinated by-products which need to be removed. One such by-product is pentachloropyridine which can be converted into 2,3,5,6-tetrachloropyridine by selective reduction of the chlorine atom in the 4-position either with zinc or electrolytically. However, zinc is expensive and large amounts of zinc salts are typically formed, a factor which is undesirable from an ecological standpoint. In addition, high-temperature chlorination, electrolytic reduction, and the generation of zinc require large amounts of energy.

U.S. Pat. No. 4,327,216 (Martin) describes a process for preparing 2,3,5,6-tetrachloropyridine and 3,5,6-trichloropyridin-2-ol by reacting trichloroacetyl chloride with acrylonitrile in the presence of a catalyst. 2,2,4-Trichloro-4-cyanobutanoyl chloride is apparently formed as an intermediate, but is not isolated. The series of reactions responsible for forming the end-products is carried out in a single operation and the combined yield of 2,3,5,6-tetrachloropyridine and 3,5,6-trichloropyridin-2-ol is not very high. Furthermore, the reaction typically produces a mixture of the two products which must be treated in subsequent operations to obtain only one of these products.

U.S. Pat. No. 4,996,323 (Pews) discloses a process for preparing 3,5,6-trichloropyridin-2-ol by conducting the following three separate reactions: trichloroacetyl chloride is added to acrylonitrile in the presence of a catalytic amount of copper or a cuprous salt to produce 2,2,4-trichloro-4-cyanobutanoyl chloride; the 2,2,4-trichloro-4-cyanobutanoyl chloride is cyclized by contacting it with acidic reagents, preferably in an anhydrous state, to form 3,3,5,6-tetrachloro-3,4-dihydropyridin-2-one; and hydrogen chloride can be eliminated from this dihydropyridinone compound to yield 3,5,6-trichloropyridin-2-ol in an aromatization reaction. However, the dihydropyridinone compound can alternatively split off water to yield 2,3,5,6-tetrachloropyridine. The water produced as a by-product during formation of the 2,3,5,6-tetrachloropyridine is a major contributor to yield loss via numerous side reactions.

U.S. Pat. No. 5,017,705 (Becker) discloses a process for producing 3,5,6-trichloropyridin-2-ol by cyclizing an aryl 4-cyano-2,2,4-trichlorobutyrate of Formula I:

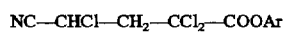

NC—CHCl—CH$_2$—CCl$_2$—COOAr     (I)

wherein Ar represents an optionally substituted aryl or heteroaryl radical, by heating the compound of Formula I to between 100° C. and 180° C. in an inert organic solvent in the presence of anhydrous hydrogen chloride to form 3,5,6-trichloropyridin-2-ol. It is taught that the presence of dry hydrogen chloride gas in the reaction medium is essential for effecting the cyclization.

U.S. Pat. No. 4,360,676 (Martin et al.) discloses that 2,3,5,6-tetrachloropyridine can be made by cyclizing 2,2,4-trichloro-4-cyanobutanecarboxamide or 2,2,4-trichloro-4-cyanobutyronitrile (2,2,4-trichloroglutaronitrile), in an aqueous acid medium, to obtain 3,3,5-trichloroglutarimide, and converting this imide compound into the desired 2,3,5,6-tetrachloropyridine product (via an aromatization reaction with dehydration of the dicarboxylic acid imide functions and simultaneous splitting-off of a hydrogen chloride group as well as a chlorination reaction). The cyclization reaction is performed at temperatures between about −10° C. and 120° C., preferably between about 60° C. and 110° C., using an acid such as acetic, hydrochloric, or sulfuric acid. The following materials are described as being suitable dehydrating, chlorinating agents for the conversion of 3,3,5-trichloroglutarimide to 2,3,5,6-tetrachloropyridine: phosphorus trichloride, phosphorus pentachloride, phosphorus oxychloride, phenylphosphonic dichloride, and phosgene. Catalytic amounts of N,N-dimethylformamide are also added to the aromatization reaction mixture under certain circumstances.

SUMMARY OF THE INVENTION

The present invention concerns a process for making 3,3,5-trichloroglutarimide by cyclizing 4-cyano-2,2,4-trichlorobutanoyl chloride. In particular, the invention relates to a process for preparing 3,3,5-trichloroglutarimide, comprising combining 4-cyano-2,2,4-trichlorobutanoyl chloride with water in an inert organic solvent at a temperature between about 20° C. and about 50° C. to obtain a mixture of 3,3,5-trichloroglutarimide and 3,3,5,6-tetrachloro-5,6-dihydropyridin-2-one, and heating the 3,3,5,6-tetrachloro-5,6-dihydropyridin-2-one in the presence of water and inert organic solvent to between about 90° C. and about 100° C. to convert the 3,3,5,6-tetrachloro-5,6-dihydropyridin-2-one to 3,3,5-trichloroglutarimide.

The process of the invention represents a different approach to making 3,3,5-trichloroglutarimide. The invention requires fewer and simpler process steps in making 3,3,5-trichloroglutarimide than prior art processes. 3,3,5-Trichloroglutarimide can be produced in high yield and without substantial amounts of by-products using starting materials which are relatively inexpensive in comparison to prior art processes for producing 3,3,5-trichloroglutarimide.

DETAILED DESCRIPTION OF THE INVENTION

The cyclization reaction of the present invention can be performed using near stoichiometric amounts of 4-cyano-2,2,4-trichlorobutanoyl chloride and water, although water is preferably used in small excess. The stoichiometric amount of water is 1 mole for each mole of 4-cyano-2,2,4-trichlorobutanoyl chloride employed. The amount of water used is important because enough water needs to be added to react with all of the 4-cyano-2,2,4-trichlorobutanoyl chloride and any impurities in the reaction mixture that are capable of reacting with water. The water needed for the conversion of 3,3,5,6-tetrachloro-5,6-dihydropyridin-2-one to 3,3,5-trichloroglutarimide can be added prior to and during the cyclization reaction or after completion of the cyclization reaction. In general, higher mole ratios of water result in faster and more complete conversions of 3,3,5,6-tetrachloro-5,6-dihydropyridin-2-one to 3,3,5-trichloroglutarimide, but water amounts which are too high lead to decreased purity of the isolated 3,3,5-trichloroglutarimide product and unidentified impurities which are difficult to separate from the 3,3,5-trichloroglutarimide. A total (for both reactions) of about 1 to about 5 moles of water are usually used for every mole of 4-cyano-2,2,4-trichlorobutanoyl chloride used. Preferably, about 1.2 moles of water are used for every mole of 4-cyano-2,2,4-trichlorobutanoyl chloride used. This water is preferably slowly added to the solution of 4-cyano-2,2,4-trichlorobutanoyl chloride in the organic solvent, i.e., prior to and during the cyclization reaction. This slow addition of water maximizes the yield and purity of the final product, 3,3,5-trichloroglutarimide.

The cyclization reaction and the reaction of 3,3,5,6-tetrachloro-5,6-dihydropyridin-2-one with water to produce additional glutarimide product generally take place in an inert organic solvent. In general, the term "inert organic solvent" is intended to denote a solvent which does not react with acid chlorides, any other initial reaction mixture ingredients, or any of the reaction products. Xylenes and tetrachloroethylene have been found to be particularly suitable solvents.

The cyclization reaction and subsequent 3,3,5,6-tetrachloro-5,6-dihydropyridin-2-one reaction with water are carried out under suitable reaction conditions. The term "suitable reaction conditions" is used herein to denote a pressure and temperature at which these two reactions can proceed substantially to completion. Although pressure is not believed to be a critical parameter, atmospheric pressure is typically employed. Also, the cyclization reaction, which is exothermic, should preferably be conducted slowly and the reaction mixture cooled so that the pot temperature can be maintained at a temperature between about 20° C. and about 50° C. The cyclization reaction time is generally a function of reaction temperature and especially of the amount of water present in the reaction vessel. However, cyclization reaction temperatures and mole ratios of water which are higher than the numbers provided above may be detrimental to the yield and/or purity of the final product. On the other hand, a cyclization reaction temperature which is too low can lead to phase separation of the reactants, resulting in no reaction at all.

The conversion of 3,3,5,6-tetrachloro-5,6-dihydropyridin-2-one to 3,3,5-trichloroglutarimide step of the process typically takes about 10 hours or more to effect high conversions. Typically, after the cyclization of 4-cyano-2,2,4-trichlorobutanoyl chloride to obtain a mixture of 3,3,5-trichloroglutarimide and 3,3,5,6-tetrachloro-5,6-dihydropyridin-2-one, the resulting mixture is heated to between about 90° C. and about 100° C. to convert the 3,3,5,6-tetrachloro-5,6-dihydropyridin-2-one to 3,3,5-trichloroglutarimide. However, it is envisioned that the 3,3,5,6-tetrachloro-5,6-dihydropyridin-2-one and/or the 3,3,5-trichloroglutarimide could be separated from that mixture using separation techniques well known in the art (e.g., recrystallization), and the 3,3,5,6-tetrachloro-5,6-dihydropyridin-2-one heated with water and inert organic solvent to between about 90° C. and about 100° C. to convert the 3,3,5,6-tetrachloro-5,6-dihydropyridin-2-one to 3,3,5-trichloroglutarimide.

The 3,3,5-trichloroglutarimide produced by the process of the invention can be recovered or employed as an intermediate in a subsequent chemical process without recovery and/or purification. For example, after the reaction of 3,3,5,6-tetrachloro-5,6-dihydropyridin-2-one with water, the reaction mixture is typically cooled, e.g., to about 20° C., and filtered to obtain a wet cake which is typically washed and dried to obtain 3,3,5-trichloroglutarimide in high yield and purity.

The 3,3,5-trichloroglutarimide can be converted to 2,3,5,6-tetrachloropyridine in accordance with procedures known in the art, e.g., as disclosed in U.S. Pat. No. 4,360,676, by treating the 3,3,5-trichloroglutarimide with a dehydrating, chlorinating agent, e.g., phosphorus oxychloride. If desired, 3,5,6-trichloropyridin-2-ol can be produced by the hydrolysis of 2,3,5,6-tetrachloropyridine as known in the art.

The following examples are presented to illustrate the invention. They should not be construed as limiting the scope of the invention. All solvents and reagents were obtained from commercial suppliers without further purification, except as noted. All parts or percentages listed are by weight unless otherwise specified.

EXAMPLES

Example 1

Preparation of 4-Cyano-2,2,4-trichlorobutanoyl Chloride

Acrylonitrile, trichloroacetyl chloride and copper were obtained from Aldrich Chemical Company. The reaction vessel was a 250 mL (milliliters) round bottom, three-necked flask equipped with a magnetic stirrer, reflux condenser, nitrogen purge, heating mantle, and thermowell. To this reaction vessel was added 45.3 g (grams) (0.86 mol) of acrylonitrile, 164.1 g (0.9 mol) of trichloroacetyl chloride, and 0.36 g (0.0057 mol) of copper. This mixture was heated under the nitrogen pad for 28 hours at reflux (the pot temperature increased as the conversion increased; when the percent conversion was in the mid 20's as determined by gas liquid chromatography ("GLC"), the reflux temperature was about 90° C., and when the percent conversion was in the mid 30's as determined by GLC, the reflux temperature was about 95°–100° C.). When the percent conversion was determined to be about 40% as determined by GLC, the system was set up for a short-path vacuum distillation, and 27 g of o-xylene was added. An extra dry ice trap was placed immediately adjacent to the distillation head to trap material that failed to condense in the distillation head. The distillation was carried out for about 1.5 hours. The pot temperature was kept at about 50°–60° C. by steadily reducing the vacuum from about 15.3 kPa (kilopascals) to about 2.0 kPa. The total distillate collected (distillate collected plus amounts in the ice trap) weighed 126.9 g. The distillate, comprising acrylonitrile and trichloroacetyl chloride, could have been recycled to improve the overall yield. The bottoms were analyzed by GLC to be sure acrylonitrile was not detected and was then diluted with 30.1 g of o-xylene and filtered. The cake was air-dried and resulted in 1.5 g of gray solids. The filtrate weighed 131.4 g and assayed at 29.2% o-xylene, 2.3% trichloroacetyl chloride, 62.7% 4-cyano-2,2,4-trichlorobutanoyl chloride, and 1.8% of various heavy organic components. The yield of recovered 4-cyano-2,2,4-trichlorobutanoyl chloride was 39%.

Example 2

Preparation of 3,3,5-Trichloroglutarimide

To a 250 mL flask was added 30 g of o-xylene and 81 g of a crude mixture comprising 64.0% 4-cyano-2,2,4- trichlorobutanoyl chloride (0.22 mol), 24.2% o-xylene, and various impurities and unreacted starting materials. This mixture was maintained at about 40°–47° C. while 4.8 g (0.27 mol) of water was slowly added to it over about 105 minutes. This resulting mixture comprised 3,3,5-trichloroglutarimide and 3,3,5,6-tetrachloro-5,6-dihydropyridin-2-one in a weight ratio of 1.3 to 1, respectively. The resulting mixture was heated and maintained at about 100° C. for about 14 hours. The mixture was then cooled to about 17° C. and filtered. The cake was washed with cold o-xylene and dried to yield 38.4 g of a tan powder that assayed at 98.2% 3,3,5-trichloroglutarimide and 0.4% 3,3,5,6-tetrachloro-5,6-dihydropyridin-2-one, resulting in a yield of 79% of isolated 3,3,5-trichloroglutarimide product. Yield losses in the filtrate were 8.8% as 3,3,5-trichloroglutarimide, 0.35% as trichloropyridinol, and 11.6% as 3,3,5,6-tetrachloro-5,6-dihydropyridin-2-one. The filtrate could have been recycled to improve the overall yield.

Various modifications and alterations of this invention will be apparent to those skilled in the art without departing from the scope and spirit of this invention.

What is claimed is:

1. A process for preparing 3,3,5-trichloroglutarimide, comprising:

(a) combining 4-cyano-2,2,4-trichlorobutanoyl chloride with water in an inert organic solvent at a temperature between about 20° C. and about 50° C. to obtain a mixture of 3,3,5-trichloroglutarimide and 3,3,5,6-tetrachloro-5,6-dihydropyridin-2-one; and (b) heating the 3,3,5,6-tetrachloro-5,6-dihydropyridin-2-one in the presence of water and inert organic solvent to between about 90° C. and about 100° C. to convert the 3,3,5,6-tetrachloro-5,6-dihydropyridin-2-one to 3,3,5-trichloroglutarimide.

2. The process of claim 1 wherein the solvent is selected from the group consisting of xylenes and tetrachloroethylene.

3. The process of claim 1 wherein about 1 to about 5 moles of water are used for every mole of 4-cyano-2,2,4-trichlorobutanoyl chloride used.

4. The process of claim 3 wherein about 1.2 moles of water are used for every mole of 4-cyano-2,2,4-trichlorobutanoyl chloride used.

5. The process of claim 1 wherein the water is added slowly to the 4-cyano-2,2,4-trichlorobutanoyl chloride.

* * * * *